United States Patent

Hagen et al.

Patent Number: 5,006,659
Date of Patent: Apr. 9, 1991

[54] PREPARATION OF 7-CHLOROQUINOLINE-8-CARBOXYLIC ACIDS

[75] Inventors: Helmut Hagen, Frankenthal; Jacques Dupuis, Ludwigshafen; Heinz Eilingsfeld, Frankenthal, all of Fed. Rep. of Germany

[73] Assignee: BASF Aktiengesellschaft, Fed. Rep. of Germany

[21] Appl. No.: 464,568

[22] Filed: Jan. 16, 1990

Related U.S. Application Data

[63] Continuation of Ser. No. 158,910, Feb. 22, 1988, abandoned.

[30] Foreign Application Priority Data

Mar. 3, 1987 [DE] Fed. Rep. of Germany ....... 3706792

[51] Int. Cl.$^5$ ............................................. C07D 215/48
[52] U.S. Cl. .................................................. 546/170
[58] Field of Search ................. 546/170, 341; 562/410

[56] References Cited

U.S. PATENT DOCUMENTS

| | | | |
|---|---|---|---|
| 3,165,548 | 1/1965 | Bartholome et al. | 546/170 |
| 4,632,696 | 12/1986 | Hagen et al. | 546/170 |
| 4,715,889 | 12/1987 | Hagen et al. | 546/170 |
| 4,804,404 | 2/1989 | Hagen et al. | 546/170 |

FOREIGN PATENT DOCUMENTS

| | | | |
|---|---|---|---|
| 565899 | 11/1958 | Canada | 562/410 |
| 0085182 | 8/1983 | European Pat. Off. | |
| 126893 | 12/1984 | European Pat. Off. | 546/170 |
| 3202736 | 8/1983 | Fed. Rep. of Germany | 546/170 |

OTHER PUBLICATIONS

"Advanced Organic Chemistry" (3rd Ed.) by Jerry March, p. 1072 (1985).
*Advanced Inorganic Chemistry* by Cotton and Wilkinson, p. 821 (3rd Ed.).

Primary Examiner—Mark L. Berch
Assistant Examiner—E. Bernhardt
Attorney, Agent, or Firm—Keil & Weinkauf

[57] ABSTRACT

7-Chloroquinoline-8-carboxylic acids of the formula (I)

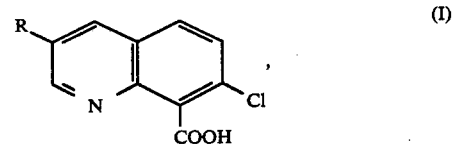

where
R is hydrogen, chlorine or methyl, are prepared by direct oxidation of the corresponding 8-methyl-qunoline compound with nitric acid or nitrogen oxide in the presence of sulfuric acid and a heavy metal catalyst.

7 Claims, No Drawings

PREPARATION OF 7-CHLOROQUINOLINE-8-CARBOXYLIC ACIDS

This application is a continuation of application Ser. No. 158,910, filed on Feb. 22, 1988, now abandoned.

The known preparation of 7-chloro-3-methylquinoline-8-carboxylic acid proceeds via the corresponding bromomethyl compound as intermediate. This process, known from EP-A-104,389, has the disadvantage that an additional reaction step and thus more resources are required, and gives the desired target product only in a low yield.

The present invention provides a process for preparing a 7-chloroquinoline-8-carboxylic acid of the formula (I)

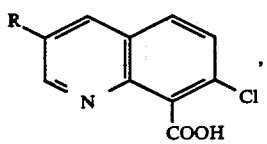

where R is hydrogen, chlorine or methyl, by direct oxidation of the corresponding 8-methylquinoline compound in the presence of sulfuric acid.

A process of this type can be put into effect by directly oxidizing the corresponding 8-methylquinoline compound with nitric acid in the presence of sulfuric acid and a heavy metal compound, ie. in the presence of a catalyst. In place of nitric acid it is also possible to use the anhydride thereof, ie. nitrogen dioxide. In every case, the spent nitric acid or nitrogen oxides can be regenerated with molecular oxygen.

The process represents a substantial improvement in respect of resource requirements and yield and purity of the target product.

Suitable heavy metals for the purposes of the present invention are in particular those whose compounds occur in a plurality of valence states, such as cobalt and vanadium. Also suitable are elements such as: manganese, iron, cerium, molybdenum, copper, ruthenium and osmium. The heavy metal compounds can be used solo or mixed. Particular effectiveness is possessed by, and preference is therefore given to, vanadium or a mixture of vanadium and cobalt. The heavy metals are preferably used, ie. added, in the form of those compounds which are soluble in sulfuric acid or mixtures of sulfuric acid and nitric acid. Compounds within this meaning are in particular the oxides and naturally the sulfates, and also the nitrates and acetates. The heavy metal is required in a catalytic amount, ie. generally in an amount of less than 10, in particular less than 5% by weight, based on the reaction mixture in which it is to act. Even very small amounts, for example less than 1% by weight, are perfectly active.

Molecular oxygen is conveniently introduced into the system in the form of air, for example by a high-speed stream, and brings about an increase in selectivity and a higher rate of reaction.

The proposed preparation can be improved in respect of resource requirements and flexibility in a particular refinement of the invention: the direct oxidation with nitric acid or with nitrogen dioxide can be carried out by recycling the $NO_x$-containing reaction off-gas. Advantageously, the off-gas is circulated and in the course of circulation is brought into contact, if desired, with molecular oxygen, ie. in practice with air, for regeneration.

The reaction is carried out at for example from 120° to 180° C., in particular at from 150° to 170° C. The 8-methylquinoline compound is present in solution in, for example, from 50 to 90% strength, preferably 70 to 85% strength, sulfuric acid, and moderately concentrated or concentrated nitric acid is used. In practice, for example, the methyl compound is introduced initially at from 150° to 160° C. in the catalyst-containing sulfuric acid, and about 3 to 6 equivalents of nitric acid, based on 1 mole of methyl compound, are then gradually added, or simply gaseous nitrogen dioxide is passed in. The saturation pressure can be atmospheric pressure or a slightly higher pressure. The reaction virtually goes to completion in the course of from 8 to 15 hours.

This is followed by dilution with water, adjustment to pH 0.5-3 (which precipitates all quinoline compounds including any byproducts), and extraction with methanol, isopropyl alcohol or the like to isolate the carboxylic acid as a residue which, if necessary, can be purified by recrystallization.

The reaction can be carried out batchwise, for example in a stirred kettle, or, in a conventional manner, continuously, using for example a stirred kettle with a downstream tubular reactor, a stirred kettle cascade or a tubular reactor; for the reaction with reactants which are supplied in gas form it is advantageous to use for example a bubble column or a gas jet reactor. Process arrangements usable here will be apparent to those trained in process engineering.

To obtain a particularly favorable result, the methyl compound is ideally as pure as possible; however, good results are also obtainable by using directly the reaction mixtures which, in sulfuric acid solution, contain a corresponding methylquinoline compound as obtained in a Skraup quinoline synthesis from an appropriately substituted toluidine and (meth)acrolein.

EXAMPLE 1

Preparation of 7-chloro-3-methylquinoline-8-carboxylic acid 191.5 g (1 mol) of 7-chloro-3,8-dimethylquinoline are dissolved in 2,400 g of 70% strength sulfuric acid, the solution is heated to 140° C., and 2.5 g of vanadium(V) oxide and 1.3 g of cobalt(II) acetate are added. 339 g of 65% strength nitric acid are added in the course of from 13 to 15 hours. The starting time for adding the nitric acid is also the starting time for introducing air. The airstream should be sufficient to remove the nitrous gases being formed. After the reaction has ended, the mixture is stirred for a further 1 to 2 hours, cooled down and diluted with water to twice the volume.

A pH of 0.5 is set with concentrated sodium hydroxide solution, and the precipitate is filtered off. A moist filtercake is twice boiled up with the same amount of methanol or isopropyl alcohol and filtered at 40° C. The acid obtained (199 g - 69% of theory) has a purity of 95%. If a higher purity is required, the alcohol treatment can be preceded by a reprecipitation from dilute sodium hydroxide solution.

EXAMPLE 2

Example 1 is repeated using exclusively 2.5 g of vanadium(V) oxide. 152 g (69%) of the target product are obtained.

EXAMPLE 3

191.5 g (1 mol) of 7-chloro-3,8-dimethylquinoline are dissolved in 1,730 g of 80% strength sulfuric acid, the solution is heated to 150° C., and 2.5 g of vanadium(V) oxide are added. 418 g of 65% strength nitric acid are added in the course of from 13 to 15 hours. The starting time for adding the nitric acid is also the starting time for pumping round, ie. circulating, the $NO_x$-containing off-gas. After the reaction has ended, the mixture is cooled down and diluted with water to twice the volume.

A pH of 0.5 is set with concentrated sodium peroxide solution, and the precipitate is filtered off. 183.3 g are obtained of a dry crude material containing 83% by weight (159 g) of quinolinecarboxylic acid (79% of theory).

EXAMPLE 4

Example 3 is repeated, except that the same amount of nitric acid is added in the course of 7 hours, affording 188.4 g of dry crude material containing 87% by weight of quinolinecarboxylic acid (74% of theory).

EXAMPLE 5

574.5 g (3 mol) of 7-chloro-3,8-dimethylquinoline are dissolved in 1,730 g of 80% strength sulfuric acid, and 7.5 g of vanadium pentoxide are added. 1,254 g of 65% strength nitric acid are added in the course of 14 hours. During this time the $NO_x$-containing off-gas is pumped round. The precipitation as in Example 1 gives 508.6 g of crude material. The quinolinecarboxylic acid content is 87% (yield 62% of theory).

EXAMPLE 6

574.5 g (3 mol) of 7-chloro-3,8-dimethylquinoline are dissolved in 1,780 g of 85% strength sulfuric acid. 10 g of vanadium pentoxide are added. At 160° C. the apparatus is saturated with $NO_2$ up to a gauge pressure of 0.2 bar. Oxygen is supplied uninterruptedly to maintain a gauge pressure of 0.5 bar; no further oxygen is absorbed after 14 hours. The reactor is let down, and the contents are worked up as described in Example 1 to give 558 g of quinolinecarboxylic acid having a purity of 89% (yield 75% of theory).

EXAMPLE 7

574.5 g (3 mol) of 7-chloro-3,8-dimethylquinoline are dissolved in 1,780 g of 85% strength sulfuric acid. 10 g of vanadium pentoxide are added. At 160° C. $NO_2$ is introduced at a rate of 200 liters per hour, and the $NO_x$-containing off-gas is pumped round. 7 hours later the reaction is complete. The reaction mixture is diluted with sodium hydroxide solution and brought to pH 0.5, and the precipitate is filtered off and dried to leave 562 g of a crude quinolinecarboxylic acid which has a purity of 87% (yield 73% of theory).

EXAMPLE 8

806 g of fully demineralized water, 2,208 g of concentrated sulfuric acid and 566 g (4 mol) of 3-chloro-2-methylaniline are introduced initially; at 40° C. a solution of 8 g of sodium iodide in 16 g of water is added. At 120° C. 336 g (4.8 mol) of methacrolein are metered in over 2 hours. 100 mg of commercial antifoam are then added, and 750 g of water are separated off azeotropically by raising the temperature to 160° C. 15 g of vanadium pentoxide are added, and gaseous $NO_2$ is introduced at a rate of 200 l/h. The reaction off-gas is pumped round, the rate of circulation being raised from 100 to 1,600 l/h in the course of 2 hours. 8 hours later the reaction is complete. Precipitation at pH 0.5 gives 727 g of a crude product having a purity of 67% (yield 54% of theory).

We claim:

1. A process for preparing a 7-chloroquinoline-8-carboxylic acid of the formula (I)

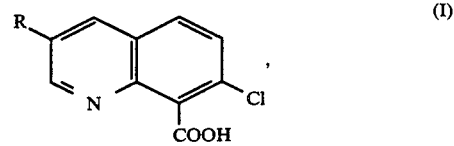

where
R is methyl, by direct oxidation of the corresponding 8-methylquinoline compound in the presence of sulfuric acid, which comprises performing the oxidation with nitric acid or nitrogen dioxide in the presence of a vanadium(V) or vanadium (IV) compound, said vanadium compound being soluble in sulfuric acid or a mixture of sulfuric acid and nitric acid.

2. The process of claim 1, wherein the reaction is carried out in the presence of, or by passing in, air.

3. The process of claim 1, wherein the oxidation is carried out with recycling of the NO and $NO_2$ containing off-gases.

4. The process of claim 3, wherein the off-gases are treated with oxygen or air.

5. The process of claim 1, wherein the vanadium compound is in the form of an oxide, a sulfate, a nitrate or an acetate.

6. The process of claim 1, wherein the vanadium compound is vanadium(V) oxide.

7. The process of claim 6, wherein said vanadium(V) oxide is in admixture with cobalt (II) acetate.

* * * * *